United States Patent
Krishna

(10) Patent No.: US 7,744,559 B2
(45) Date of Patent: Jun. 29, 2010

(54) SYSTEMS AND METHODS FOR DRUG INFUSION WITH FEEDBACK CONTROL

(75) Inventor: Suhas Krishna, Campbell, CA (US)

(73) Assignee: Cytyc Corporation, Marlborough, MA (US)

( * ) Notice: Subject to any disclaimer, the term of this patent is extended or adjusted under 35 U.S.C. 154(b) by 87 days.

(21) Appl. No.: 11/959,143

(22) Filed: Dec. 18, 2007

(65) Prior Publication Data

US 2008/0146993 A1 Jun. 19, 2008

Related U.S. Application Data

(60) Provisional application No. 60/870,676, filed on Dec. 19, 2006.

(51) Int. Cl.
*A61M 31/00* (2006.01)
(52) U.S. Cl. ..................................... 604/65; 604/96.01
(58) Field of Classification Search ................... 604/65, 604/117, 264, 96.01–109; 600/429; 606/192, 606/194, 200
See application file for complete search history.

(56) References Cited

U.S. PATENT DOCUMENTS 5,720,720 A * 2/1998 Laske et al. ................. 604/500
5,891,089 A * 4/1999 Katz et al. ................. 604/97.01
6,105,582 A * 8/2000 Pranevicius et al. ......... 128/898
2004/0127813 A1* 7/2004 Schwamm ................... 600/561
2006/0079857 A1* 4/2006 Putz ........................... 604/500

FOREIGN PATENT DOCUMENTS

EP 0 581 708 2/1994

* cited by examiner

*Primary Examiner*—Nicholas D Lucchesi
*Assistant Examiner*—Gerald Landry, II
(74) *Attorney, Agent, or Firm*—Marc A. Vivenzio; Lindsay McGuiness

(57) ABSTRACT

A system and method for infusing a drug under continuous positive pressure (such as convection enhanced deliver) to a target tissue to be treated is particularly useful for post-resection anticancer drug therapy. The system comprises a drug infusion catheter having an expandable device which is expanded within the target tissue such that the target tissue conforms to an outer surface of the expandable device, thereby creating a form of seal around the target volume in order to maintain an effective drug pressure gradient within the target tissue. The system further comprises a sensor to measure a parameter which can be correlated to the degree of conformance between the target tissue and the outer surface of the expandable device. The sensor is coupled to a feedback control system to determine whether there is a loss of conformance, and to adjust the expansion of the expandable device in order to maintain good conformance.

9 Claims, 6 Drawing Sheets

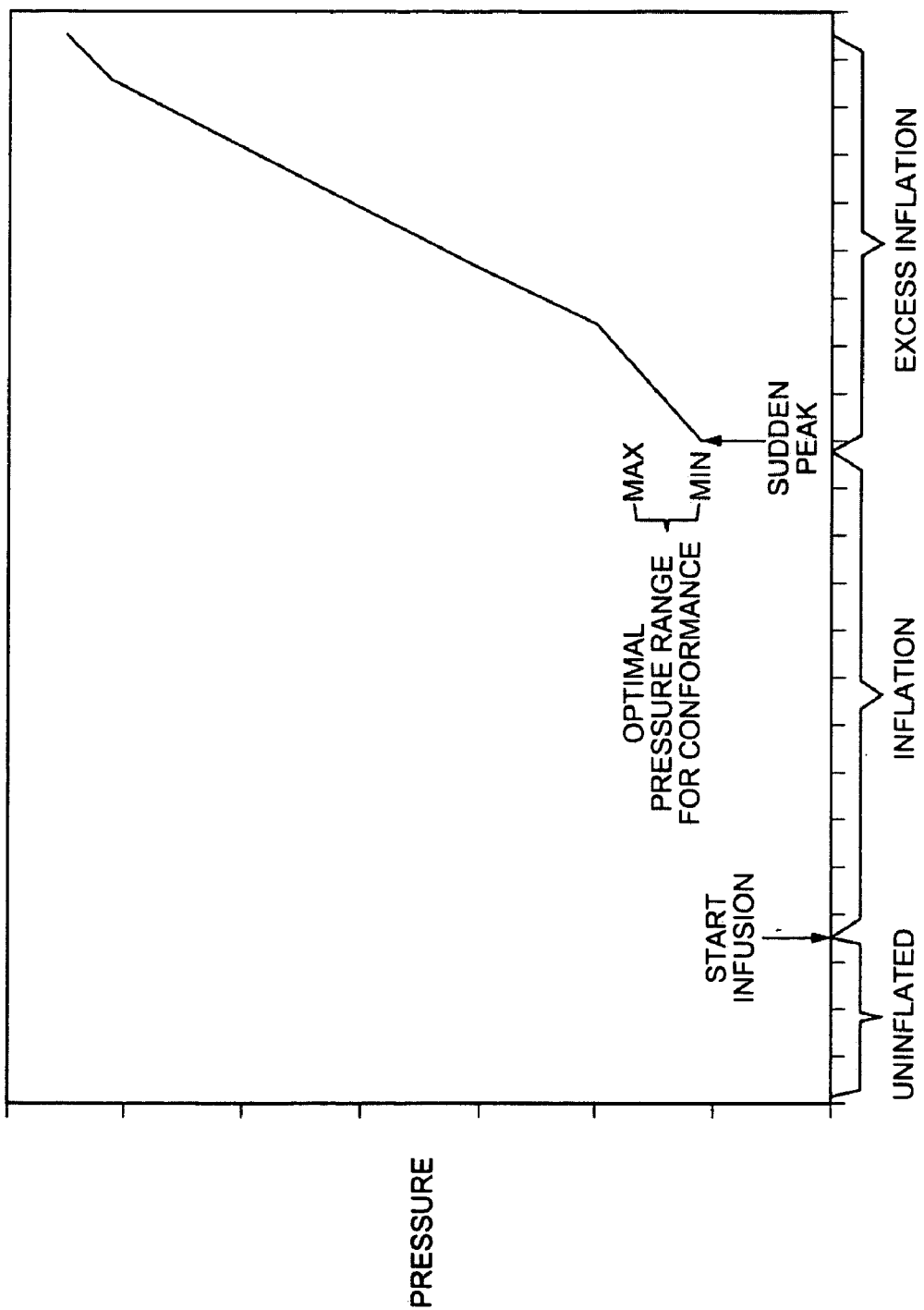

SYSTEMS AND METHODS FOR DRUG INFUSION WITH FEEDBACK CONTROL

FIELD OF THE INVENTION

The present invention relates generally to devices and methods for use in directly delivering drugs to tissue within a patient's body, and more particularly to devices and methods for the continuous drug infusion directly to target tissue with feedback control of the infusion pressure.

BACKGROUND OF THE INVENTION

Malignant tumors are often treated by surgical resection of the tumor to remove as much of the tumor as possible. Infiltration of the tumor cells into normal tissue surrounding the tumor, however, can limit the therapeutic value of surgical resection because the infiltration can be difficult or impossible to treat surgically. Direct chemo-drug (anticancer drug) delivery therapy and radiation therapy are the two common post-resection treatment methods used to supplement surgical resection by targeting the residual malignant cells after resection, with the goal of sterilizing them, reducing the rate of recurrence, and/or delaying the time to recurrence. Radiation therapy can be administered through one of several methods, or a combination of methods, including permanent or temporary brachytherapy implants, and external-beam radiation. Direct chemo-drug delivery therapy is typically administered by inserting a catheter device into the resected cavity and infusing chemo-drugs through a lumen in the catheter and into the resected cavity where the drugs diffuse into the surrounding tissue. In some cases, direct chemo-drug therapy is applied to a tumor without resection in order to shrink the tumor prior to resection, or in the case of where surgery is contraindicated (e.g. inoperable tumors).

However, in certain treatment areas of the body, it is very difficult for the drugs to penetrate the target tissue (either a tumor itself, or the tissue surrounding the area of a resected tumor). For example, it is difficult for large molecule drugs to penetrate the brain parenchyma when treating brain tissue. Thus, in these situations, the chemo-therapy does not treat a sufficient thickness of tissue (typically 1-2 cm) to target the residual malignant cells. In order to improve drug penetration in these types of situations, a method of directly delivering the drugs to the target tissue under positive pressure has been developed. This method is commonly referred to as convection-enhanced delivery (CED). CED uses continuous positive pressure drug infusion to generate a pressure gradient to cause the drug to diffuse into the desired thickness of target tissue.

However, current methods and devices have several drawbacks. For one, at some point during infusion, the drugs tend to leak out of the target volume (the volume of target tissue) through the space in the tissue created by the catheter. The drugs can then follow the catheter pathway through the tissue and out of the patient's body. Moreover, once this occurs, it is difficult to maintain the pressure gradient within the target volume resulting in ineffective drug penetration into the target tissue.

Accordingly, there remains a need for methods and devices which can provide for effective direct delivery of drugs under continuous positive pressure drug infusion.

SUMMARY OF THE INVENTION

The present invention provides devices and methods for use in providing direct delivery of drugs under continuous positive pressure drug infusion. In one aspect, a drug infusion catheter comprises an elongate tubular member having a distal portion which is adapted to be inserted within a patient's body to a treatment site having a target volume of target tissue to be treated. The tubular member has a proximal portion and a proximal end which are adapted to extend out of the patient. An expandable device is provided on the distal portion of the tubular member and a hub is provided on the proximal end of the tubular member. The expandable member has a contracted position and an expanded position.

The tubular member has a drug delivery lumen which extends from a drug delivery outlet (the outlet can comprise one or more outlet openings) provided on the distal portion of the tubular member to a drug infusion port provided on the hub. The tubular member also has an inflation lumen (or expansion link, depending on the configuration of the expandable device) which extends from the expandable device to an inflation port on the hub.

The method of using the infusion catheter comprises first inserting the catheter, with the expandable device in its contracted position, into a resected space within the target volume of target tissue. The expandable device is then expanded to its expanded position, for example, by delivering a source of pressurized inflation fluid through the inflation port and into the expandable device. The tissue surrounding the expandable device con forms to the surface of the expandable device which, at least to some extent, seals the space in the tissue through which the catheter extends. Now, drug is infused through the drug infusion port at a continuous positive pressure. The drug travels through the infusion lumen, out of the delivery outlet and into the target tissue. The expandable device provides a sealing effect to the space such that an effective drug pressure gradient is maintained in the target volume. The drug is continuously infused at a positive pressure for a relatively long period of time, for example, at least 3 hours, 6 hours, 1 day, 2 days, 3 days, or more.

In another aspect of the present invention, a feedback control system is provided which controls the expansion of the expandable device in order to maintain conformance of the expandable device with the surrounding tissue in order to maintain an effective seal between the expandable device and the target volume. In one aspect of the feedback control system, the feedback control system measures certain parameters related to the drug infusion procedure which can be correlated to the conformance of the expandable device to the surrounding tissue, such as balloon pressure, force at the expandable device/tissue interface, drug infusion pressure within the infusion pump or catheter lumen, and/or the drug infusion pressure in the target volume. The feedback control system then correlates one or more of these measured parameters to the degree of conformance between the expandable device and the tissue and uses the measured parameter(s) and the correlated conformance to adjust the volume of the expandable device.

BRIEF DESCRIPTION OF THE DRAWINGS

In order to better understand and appreciate the invention, reference should be made to the drawings and accompanying detailed description, which illustrate and describe exemplary embodiments thereof. For ease in illustration and understanding, similar elements in the different illustrated embodiments are referred to by common reference numerals, and the description for such elements shall be applicable to all described embodiments, wherever relevant. In particular:

FIG. 5 is an exemplary graph of pressure within a balloon as it is inflated within a resected cavity, in which the graph shows inflection points which can be correlated to conformance of the balloon with the surrounding tissue;

FIGS. 6a and 6b are exemplary graphs of drug infusion pressure showing the pressure during an infusion process, in which FIG. 6a shows a stabilized pressure indicating good conformance maintained between the balloon and tissue and FIG. 6b shows a drop in pressure indicating a loss of conformance between the balloon and the tissue;

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Figure 1:
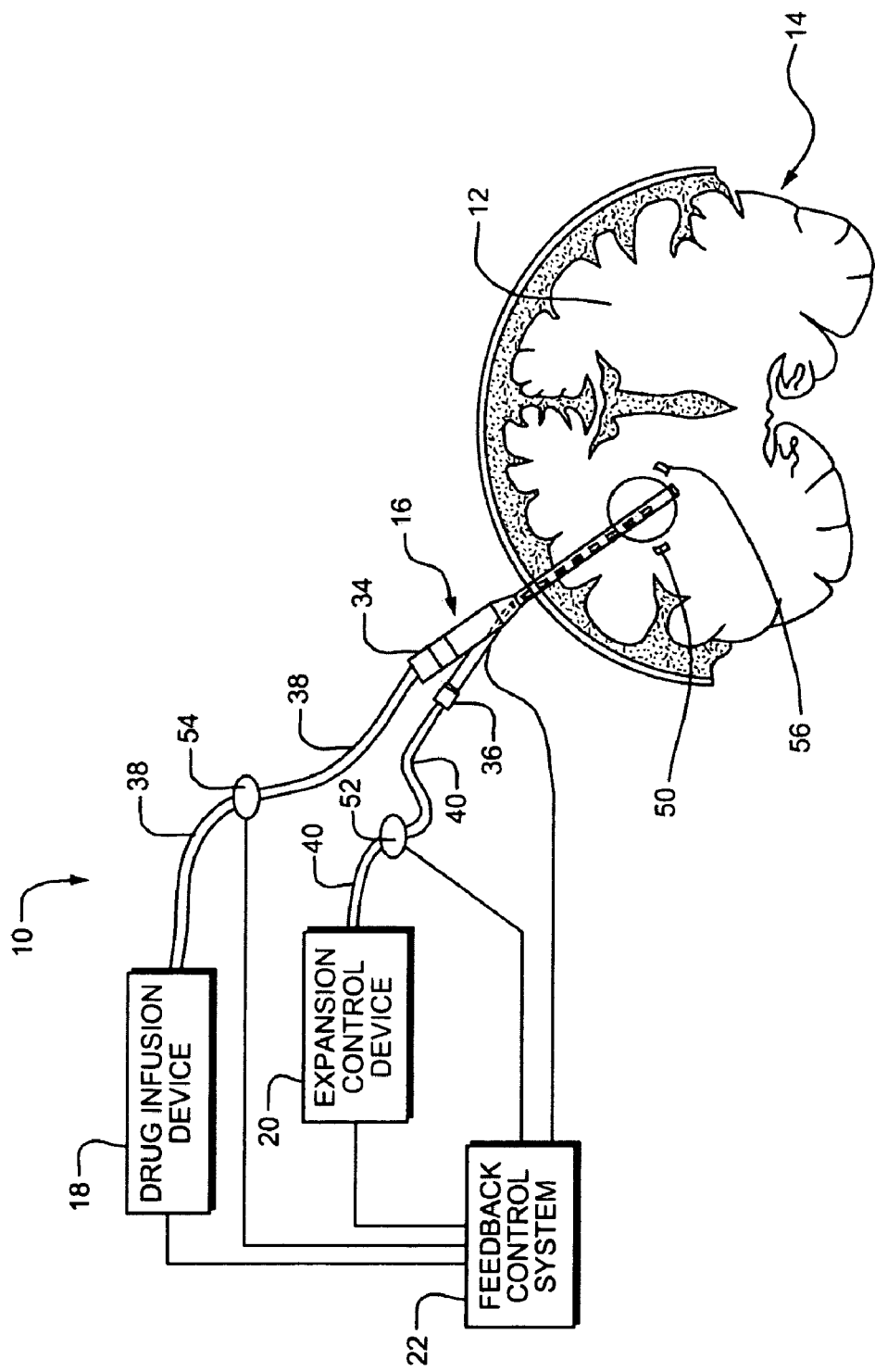
FIG. 1 is a schematic view of an exemplary drug infusion system according to the present invention.

Referring first to FIG. 1, a drug infusion system 10 having feedback control according to the present invention is schematically illustrated. The drug infusion system 10 will be described in reference for infusing drug to tissue 12 within a brain 14, with the understanding that the present invention is not limited to procedures within the brain, but can be used for drug infusion to tissue anywhere in a patient's body. The drug infusion system 10 comprises a drug infusion catheter 16, which is operably coupled to a drug infusion device 18, an expansion control device 20 and a feedback control system 22.

Figure 2:
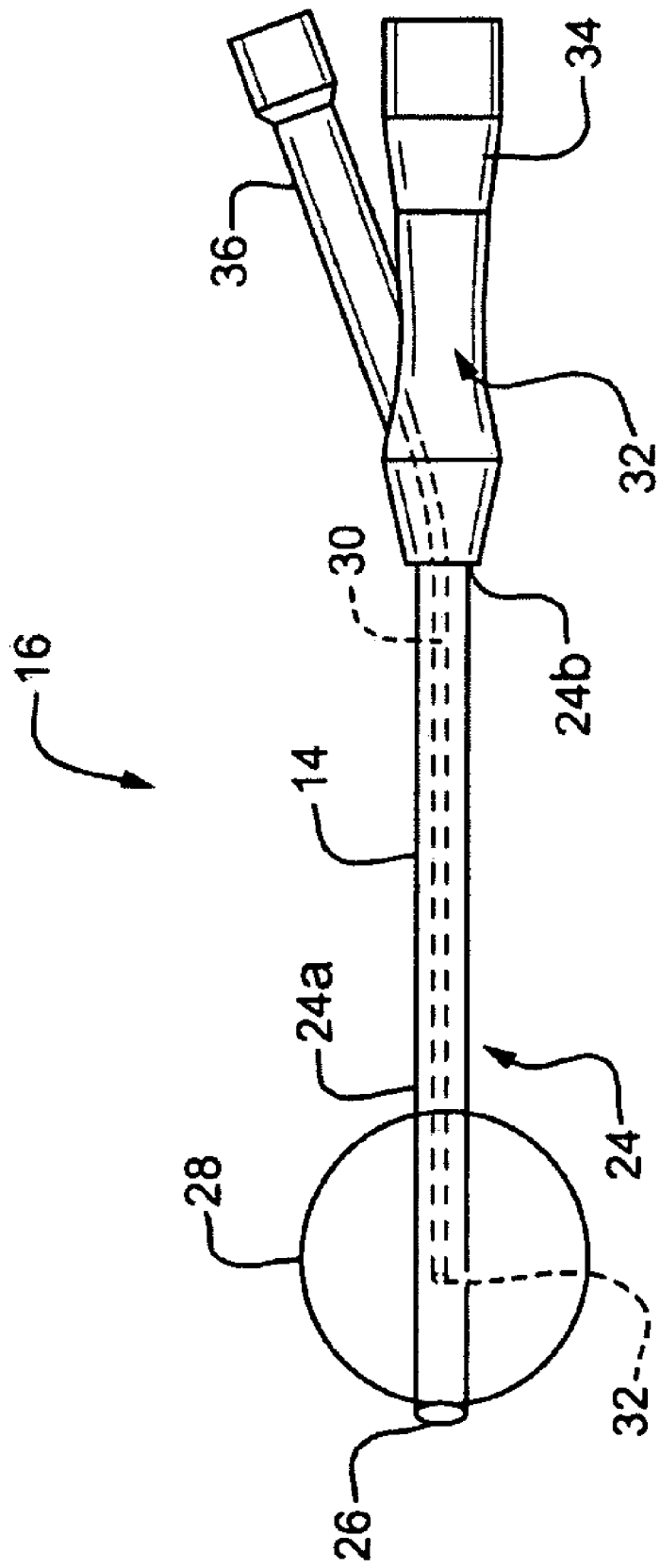
FIG. 2 is an enlarged, side, schematic view of the drug infusion catheter of FIG. 1.

With reference also to the enlarged view of FIG. 2, the drug infusion catheter 10 comprises an elongate tubular member 24 having a distal portion 24a and a proximal portion 24b, and a main lumen 14 extending therebetween. The distal portion 24a is adapted to be inserted into the patient's body to the treatment location comprising a target volume of target tissue. The proximal end 24b is adapted to extend outside the patient's body. The walls of the tubular member 24 are substantially impermeable to fluids, except for any intended apertures and openings in the walls of the tubular member.

The distal portion 24a of the tubular member 24 has a drug delivery outlet 26 which is in fluid communication with the main lumen 14. The drug delivery outlet 26 may comprise a single opening, as shown, or it may comprise multiple openings which are spaced apart about the distal portion 24a of the tubular member 24.

An expandable device 28 is provided on the distal portion 24a of the tubular member 24. The expandable device 28 can be any device which can be controllably expanded and contracted to retract tissue, such as a balloon, a cage, or other device. The expandable device 28 can have any suitable shape, including for example, spherical, oblong, etc. An expansion link 30, such as a balloon inflation lumen, is disposed within the main lumen 14 and extends from the expandable device 28 to the proximal end 24a of the tubular member 24. Depending on the form of the expandable device 28, the expansion link 30 could comprise a mechanical linkage, an electrical connection, or other suitable link for remotely expanding and contracting the expandable device 28. Alternatively, the expansion link 30 can be provided on the exterior of the tubular member 24, or it can be integrally formed with the tubular member 24. The expansion link 30 allows the expandable device 28 to be controllably expanded and contracted through the link 30, such as by delivering an inflation fluid to a balloon through an inflation lumen. In order to simplify the following description, the expandable device 28 will be assumed to be a balloon 28 and the expansion link 30 will be assumed to be an inflation lumen 30, with the understanding that the present invention is not limited to a balloon and an inflation lumen, as discussed above. Accordingly, the distal end of the inflation lumen 30 has an inflation fluid port 32 which is in fluid communication with the balloon 28.

A hub 32 is disposed on the proximal end 24b of the tubular member 24. The hub 32 has a drug delivery port 34 and an inflation port 36. The drug delivery port 34 is in fluid communication with the main lumen 14. The inflation port 36 is in fluid communication with the inflation lumen 30.

The hub 32 may be formed in any suitable fashion as known by those skilled in the art. For example, the hub 32 may be integrally formed of plastic or other suitable material. Moreover, the hub 32 may include additional ports, as needed for the particular application of the catheter 16. For instance, the catheter 16 could have more than one balloon, wherein each of the balloons is independently inflatable. Thus, the hub 32 could have an additional port for each additional balloon.

Turning back to FIG. 1, the drug delivery port 34 on the catheter 16 is connected to one end of a drug supply tube 38. The other end of the drug supply tube 38 is connected to the drug infusion device 18. The drug infusion device 18 is adapted to controllably provide a supply of drug, typically in fluid form, through the supply tube 38 to the drug delivery port 34 on the catheter 16. The drug infusion device can be, for example, a syringe pump, other automated drug pump, or even a manual syringe. The inflation port 36 on the catheter is connected to one end of an inflation tube 40 and the other end of the inflation tube 40 is connected to the expansion control device 20. The expansion control device 20 is adapted to controllably expand and contract the expandable device 28, which for the balloon embodiment, comprises supplying a pressurized inflation fluid. The expansion control device 20 may provide the pressurized inflation fluid using a syringe pump, or any other suitable device for supplying a source of pressurized fluid.

Figure 3:
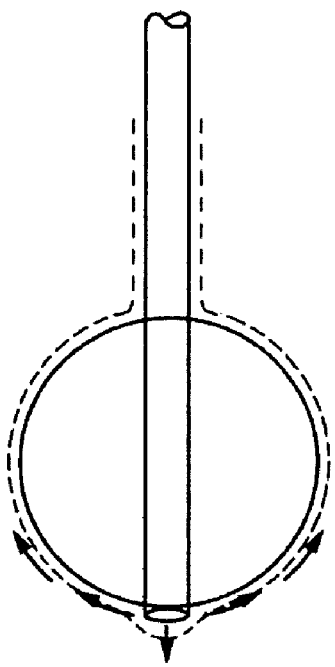
FIG. 3 is an enlarged schematic view of the balloon and tissue region of FIG. 1 which depicts the drug flow when there is good conformance between the expandable device and the surrounding tissue.
Figure 4:
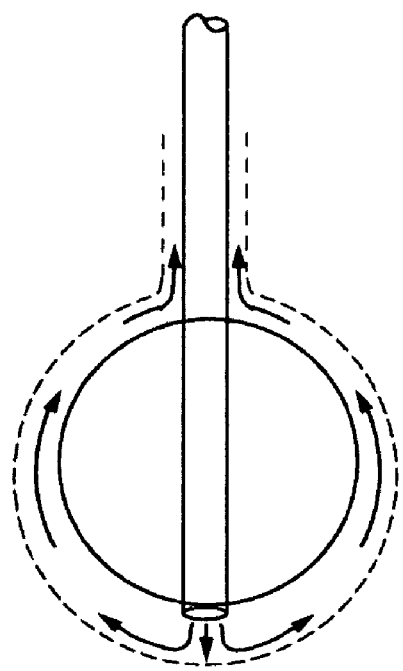
FIG. 4 is an enlarged schematic view of the balloon and tissue of FIG. 1 which depicts the drug flow when there is loss of conformance between the expandable device and the surrounding tissue.

One objective of the system 10 according to the present invention is to utilize feedback control in order to maintain effective drug pressure gradient during an infusion procedure. As discussed above, a loss in conformance can cause a degradation of the drug infusion pressure gradient resulting in ineffective drug penetration into the target tissue. This condition is graphically illustrated in FIGS. 3 and 4. The dashed lines in FIGS. 3 and 4 depict the border of the tissue 12 surrounding the balloon 28 and the arrows depict the drug flow. As shown in FIG. 3, the tissue 12 is conforming very well to the balloon 28 and the drug flow shows effective penetration into the target tissue. On the other hand, in FIG. 4, the tissue has moved away from the balloon 28 and has lost conformance. As a result, there is significant backflow of the drug out of the resected space and a loss of drug pressure gradient resulting in ineffective drug penetration into the target tissue.

In order to provide the feedback control according to the present invention, the system 10 comprises one or more sensors to measure various parameters of the operation of the system 10 which can be correlated to conformance of the balloon 28 and the surrounding tissue 12. The feedback control allows the system 10 to adjust for a loss in conformance between the inflated balloon 28 and the surrounding tissue in the resected cavity. The system 10 in FIG. 1 includes a plurality of sensors, however, as described below, the system 10 according to the present invention need only have any one of the sensors, and can have any combination of two or more of the sensors.

The system 10 includes a force sensor 50, a balloon pressure sensor 52, a drug infusion pressure sensor 54, and a drug diffusion pressure sensor 56. Each of the sensors, 50, 52, 54 and 56, is operably coupled to the feedback control system 22 to transmit s signal to the feedback control system indicative of the parameter measured by the respective sensors.

The force sensor 50 is a force sensor which is placed between the surface of the balloon 28 and the surrounding tissue 12 to measure the force between the surface of the balloon 28 and the surrounding tissue 12. The sensor 50 quite directly measures the conformance of the tissue 12 to the balloon 28. Thus, the correlation between this measured parameter of force between the balloon 28 and the tissue 12 is as follows. With the balloon 28 first located in a resected cavity with the balloon uninflated, the sensor 50 will measure little or no force. As the balloon 28 is inflated, at some point in the inflation the balloon will push the sensor 50 into the wall of tissue 12 and the sensor 50 will indicate a sharp increase in force. As the balloon 28 is further inflated, the sensor 50 will indicate a continued increase in force. When the inflation is stopped, the sensor 50 will indicate a relatively constant force. As the infusion process continues, the tissue may compress away from the sensor 50, which will be indicated by a drop in the force as measured by the sensor 50. This will indicate a decrease in the conformance of the balloon 28 to the tissue 12. The feedback control system 20 is adapted to detect this decrease, and will adjust the balloon 28 inflation accordingly.

Multiple force sensors 50 may be utilized, such that multiple locations around the interface between the balloon 28 and the tissue 12 may be detected. In this way, the feedback control system 20 can detect the conformance at multiple points and adjust the volume of the balloon 28 to maintain the desired level of conformance.

The balloon pressure sensor 52 is a pressure sensor which measures the pressure of the inflation fluid in the balloon 28. The balloon pressure sensor 52 may be placed in-line of the inflation tube 40, or even directly within the balloon 28. The correlation between the balloon pressure sensor and the conformance of the balloon 28 and the tissue 12 is similar to that of the force sensor. With the balloon 28 first located in a resected cavity with the balloon uninflated, the sensor 52 will measure little or no force. As soon as balloon 28 inflation starts, the sensor 52 will measure an increase in pressure. As the balloon 28 is further inflated, the sensor 52 will indicate a continued increase in pressure. When the inflation is stopped, the sensor 52 will indicate a relatively constant force. If, during the infusion process, the balloon 28 begins to lose conformance with the tissue, the pressure indicated by the sensor 52 will decrease. A drop in pressure can be correlated to a decrease in the conformance of the balloon 28 to the tissue 12. FIG. 5 shows an exemplary graph of the pressure readings of a balloon pressure sensor 52 as it is inflated in a tissue cavity. FIG. 5 shows the pressure increasing at the start of the inflation process. Then, there is a range of pressure which is considered to be optimal for balloon conformance. Less than good conformance is indicated if the pressure measured by the sensor 52 is lower than the optimal range. Excess pressure may be indicated if the sensor 52 measures a pressure labeled as excess inflation pressure in FIG. 5. The feedback control system 20 is adapted to detect the pressure reading from sensor 52, and to adjust the balloon 28 inflation accordingly.

Figure 6B:
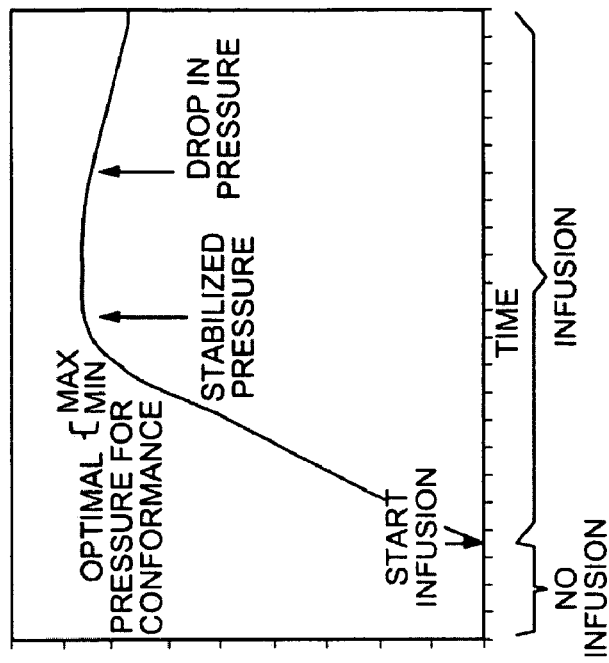
Figure 6A:
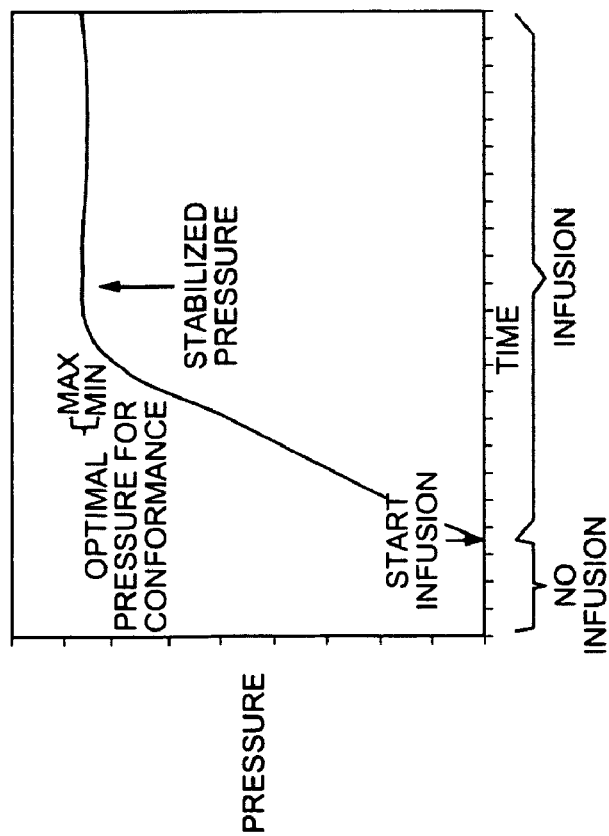

The drug infusion pressure sensor 54 is a pressure sensor which measures the pressure of the drug fluid being infused through the catheter 16 (back pressure). The drug infusion pressure sensor 54 is placed in-line of the drug infusion tube 40, but may also be placed anywhere else along the drug infusion pathway. The correlation between the drug infusion pressure sensor 54 and the conformance of the balloon 28 and the tissue 12 is generally as follows. With the balloon 28 located in the resected cavity and the balloon 28 properly inflated, the drug infusion device 18 is operated to supply drug, in fluid form, to the drug delivery port 34 on the infusion catheter 16 The infusion catheter 16 directs the drug to the target volume of tissue 12. When the drug is first delivered, the pressure in the delivery line, as measured by the sensor 54, will gradually increase as the tubes and lumens are filled with drug and are pressurized, until a steady state pressure is achieved. As long as balloon/tissue conformance is maintained, the pressure measured by sensor 54 will remain relatively stable. If there is a loss in conformance, the drug infusion pressure at the sensor 54 will drop as the relative volume in the cavity increases. Thus, a drop in pressure detected by sensor 54 can be correlated to a decrease in the conformance of the balloon 28 to the tissue 12. FIGS. 6a and 6b show exemplary graphs of the pressure readings of a drug infusion pressure sensor 54 during a drug infusion procedure. FIG. 6a shows a stabilized pressure indicating good conformance, while FIG. 6b shows a drop in pressure indicating a loss of conformance. FIGS. 6a and 6b also illustrate an exemplary range of optimal acceptable pressure drop which correlates to good balloon conformance. Any drop in pressure below the threshold amount may be used to indicate excessive loss of conformance. Upon detecting the threshold amount of pressure drop at sensor 54, the feedback control system 20 is adapted to adjust the balloon 28 inflation accordingly.

The drug diffusion pressure sensor 56 is a pressure sensor which measures the pressure of the drug fluid at or near the target tissue. For example, the drug infusion pressure sensor 56 may be placed at the outside surface of the balloon 28 at a spaced apart location from the drug delivery outlet 26. The correlation between the drug diffusion pressure sensor 56 and the conformance of the balloon 28 and the tissue 12 is substantially the same as the drug infusion pressure sensor 43. Indeed, a graph of the pressure readings of a drug diffusion pressure sensor 56 during a drug infusion procedure would look very similar to those of FIGS. 6a and 6b, except that the magnitude of the pressures would be less. In the same way as for the drug infusion pressure sensor 54, upon detecting a threshold amount of pressure drop at sensor 56, the feedback control system 20 is adapted to adjust the balloon 28 inflation accordingly.

Figure 7:
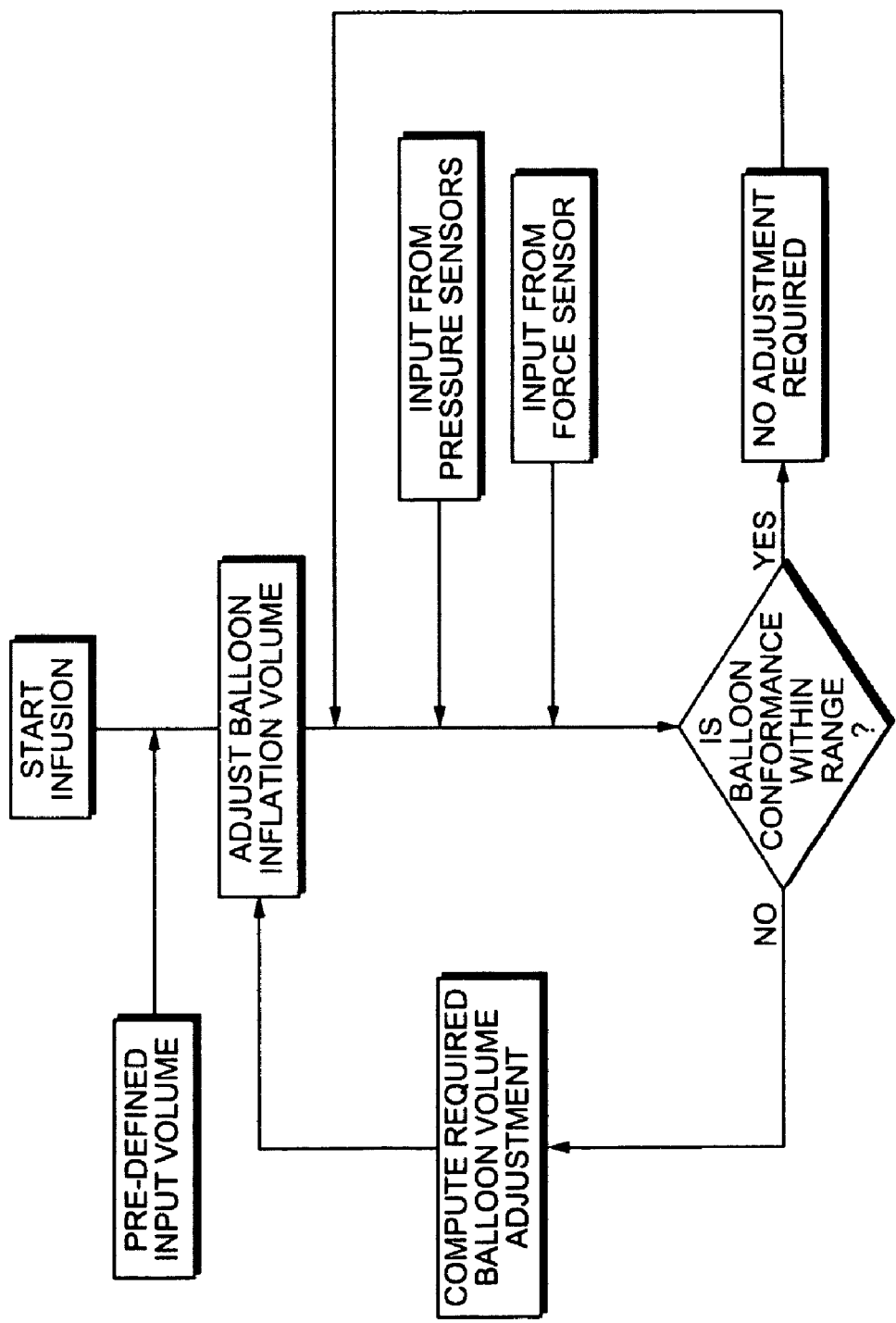
FIG. 7 is a flow chart of an exemplary algorithm used by the Feedback Control System of FIG. 1, according to the present invention.

The feedback control system 22 is operably coupled to each of the sensors 50, 52, 54 and 56 and receives input signals from these sensors. In one implementation of the feedback control system, the feedback control system computes the inflation volume of the balloon 28 based on the input from the sensors 50, 52, 54 and 56 and a pre-defined set of algorithms. Then, the feedback control system computes the necessary adjustment to the inflation volume of the balloon 28 in order to provide the desired conformance of the balloon 28. The feedback control system 22 is operably coupled to the expansion control device 20 so that the feedback control system 22 can control the expansion control device 20 to adjust the inflation volume of the balloon 28. As the inflation volume of the balloon 28 is adjusted, the feedback control system continues to receive input signals from the sensors, which can be used to re-compute the inflation volume of the balloon 28 and/or the required adjustment to the inflation volume. This forms the closed-loop control system of the present invention. A flow chart for an exemplary algorithm by which the feedback control system 22 may operate is shown in FIG. 7.

As mentioned above, any one or more of the sensors 50, 52, 54, and 56 may be used in the system 10. In one exemplary implementation, only the balloon inflation pressure sensor 52 and the force sensor 50 are used. In another exemplary implementation, only the drug infusion pressure sensor 54 and the drug diffusion pressure sensor 56 are utilized. In still another implementation, only one of the sensors 50, 52, 54 and 56 are utilized and one or more of the other parameters is determined using a pre-defined correlation between the measured parameter and the other parameters. For example, the system 10 may utilize only the drug infusion pressure sensor 54, such the system 10 can effectively monitor and adjust conformance using only a single parameter.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method of infusing a drug to a target tissue within a target volume, comprising the following steps:
    inserting an expandable device defining an outer surface into the target volume;
    inserting at least one sensor between (i) said outer surface of the expandable device and (ii) the tissue in the target volume directly adjacent to and surrounding said outer surface of said expandable device;
    expanding said expandable device such that the surrounding tissue in the target volume conforms to said outer surface of said expandable device such that at least a portion of said outer surface of said expandable device and an area of the target tissue define an enclosed treatment volume;
    delivering a drug under a continuous positive pressure to said enclosed treatment volume;
    measuring a parameter which can be correlated to the degree of conformance between said outer surface of said expandable device and the tissue in the target volume directly adjacent to and surrounding said expandable device; and
    adjusting the volume of said expandable device based on said measured parameter.

2. The method of claim 1, wherein said expandable device is disposed on an infusion catheter comprising a elongate tubular member having a distal portion adapted to be inserted within a patient's body and a proximal portion which is adapted to extend out of the patient, wherein said expandable device is located on said distal portion.

3. The method of claim 1, wherein said parameter is one of a drug infusion pressure, a drug diffusion pressure, an inflation pressure of said expandable device, or a force between said outer surface of said expandable device and the surrounding tissue.

4. The method of claim 1, wherein said expandable device is a balloon.

5. The method of claim 1, further comprising the following steps:
    receiving a signal corresponding to the measured parameter at a feedback control system;
    analyzing the measured parameter at said feedback control system to determine whether there is an excessive loss of conformance; and
    adjusting the volume of said expandable device if it is determined that there is an excessive loss of conformance.

6. A system for infusing a drug to a target tissue within a target volume, comprising:
    a drug infusion catheter comprising
        an elongate tubular member having a distal portion adapted to be inserted within a patient's body and a proximal portion which is adapted to extend out of the patient;
        an expandable device disposed on said distal portion, said expandable device having an outer surface that is expandable within the target tissue such that the target tissue conforms to said outer surface; and
        a drug delivery outlet disposed on said distal portion which is adapted to dispense a drug into the target tissue;
    an expansion control device operably coupled to said infusion catheter such that it can be operated to control the volume of said expandable device;
    at least one sensor for measuring a parameter which can be correlated to the degree of conformance between said outer surface of the expandable device and the tissue in the target volume directly adjacent to and surrounding said expandable device, wherein the at least one sensor is positioned between (i) said outer surface of the expandable device and (ii) the tissue in the target volume directly adjacent to and surrounding said outer surface of said expandable device;
    a drug delivery device for delivering a drug under continuous positive pressure to said drug infusion catheter; and
    a feedback control device operably coupled to said at least one sensor and to said expansion control device, said feedback control device being adapted to receive a signal from said sensor indicative of the sensor measurement of said parameter, to use said signal to determine whether there is an excessive loss of conformance between said outer surface of the expandable device and the tissue in the target volume directly adjacent to and surrounding the expandable device, and to control said expansion control device to adjust the volume of said expandable device based on the determination of whether there is an excessive loss of conformance.

7. The system of claim 6, wherein said expandable device is a balloon.

8. The system of claim 6, wherein said parameter is one of a drug infusion pressure, a drug diffusion pressure, an inflation pressure of said expandable device, or a force between said outer surface of said expandable device and the surrounding tissue.

9. The system of claim 6, further comprising one or more additional sensors, each additional sensor for measuring a parameter which can be correlated to the degree of conformance between said outer surface and the surrounding tissue, wherein each of said additional sensor is operably coupled to said feedback control system.

* * * * *